(12) United States Patent
Duranton et al.

(10) Patent No.: US 9,012,418 B2
(45) Date of Patent: Apr. 21, 2015

(54) TOPICAL ADMINISTRATION OF AT LEAST ONE DOUBLE-STRANDED RNA OLIGONUCLEOTIDE (DSRNA)

(75) Inventors: Albert Duranton, Maison Laffite (FR); Christine Collin-Djangone, Amblainville (FR); Francis Pruche, Senlis (FR); Jean-Thierry Simonnet, Paris (FR)

(73) Assignee: L'Oreal, Paris (FR)

( * ) Notice: Subject to any disclaimer, the term of this patent is extended or adjusted under 35 U.S.C. 154(b) by 374 days.

(21) Appl. No.: 12/007,387

(22) Filed: Jan. 9, 2008

(65) Prior Publication Data

US 2009/0117063 A1 May 7, 2009

Related U.S. Application Data

(63) Continuation of application No. 11/001,085, filed on Dec. 2, 2004, now abandoned, which is a continuation of application No. PCT/FR03/01648, filed on Jun. 2, 2003.

(30) Foreign Application Priority Data

Jun. 3, 2002 (FR) .................................. 02 06796

(51) Int. Cl.
| | |
|---|---|
| A61K 48/00 | (2006.01) |
| C07H 21/02 | (2006.01) |
| C07H 21/04 | (2006.01) |
| A61K 8/60 | (2006.01) |
| A61K 31/7088 | (2006.01) |
| A61Q 7/00 | (2006.01) |
| A61Q 19/00 | (2006.01) |
| A61Q 19/02 | (2006.01) |
| A61Q 19/08 | (2006.01) |

(52) U.S. Cl.
CPC .............. *A61Q 19/007* (2013.01); *A61K 8/606* (2013.01); *A61K 31/7088* (2013.01); *A61Q 7/00* (2013.01); *A61Q 19/00* (2013.01); *A61Q 19/02* (2013.01); *A61Q 19/08* (2013.01); *C12N 2310/13* (2013.01)

(58) Field of Classification Search
None
See application file for complete search history.

(56) References Cited

U.S. PATENT DOCUMENTS

| | | | | |
|---|---|---|---|---|
| 5,780,607 | A  * | 7/1998 | Goodnow et al. | 536/22.1 |
| 6,506,559 | B1 * | 1/2003 | Fire et al. | 435/6 |
| 2003/0125281 | A1 * | 7/2003 | Lewis et al. | 514/44 |
| 2005/0002917 | A1 * | 1/2005 | Schwartz et al. | 424/93.21 |

OTHER PUBLICATIONS

Opalinska et al. (Nature Reviews Drug Discovery, 2002, vol. 1, p. 503-514).*
Elbashir et al. (Nature 2001, vol. 411, pp. 494-498).*
Bass (Nature 2001, vol. 411, pp. 428-429).*

* cited by examiner

*Primary Examiner* — Amy Bowman
(74) *Attorney, Agent, or Firm* — Buchanan Ingersoll & Rooney PC (57) ABSTRACT

Expression of a messenger RNA which encodes a protein which is expressed by differentiated cells, notably the cells of the skin or appendages thereof, is inhibited by topically administering to said differentiated cells a thus effective amount of at least one double-stranded RNA oligonucleotide, formulated into a topically applicable, physiologically acceptable medium therefor; such regime or regimen is useful for treating a variety of afflictions or conditions, e.g., combating the signs of skin aging, stimulating hair growth or retarding loss thereof, inhibiting cellular proliferation and/or differentiation, etc.

21 Claims, 2 Drawing Sheets

```
                          SEQUENCE LISTING

<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
ugcaccacuu gggccucaat t                                                  21

<210> SEQ ID NO 2
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
uugaggccca aguggugcat t                                                  21

<210> SEQ ID NO 3
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 3
cggcuacgac cccguaaact t                                                  21

<210> SEQ ID NO 4
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 4
guuuacgggg ucguagccgt t                                                  21

<210> SEQ ID NO 5
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
agccgcgagg gucguccaat t                                                  21

<210> SEQ ID NO 6
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
uuggacgacc cucgcggcut t                                                  21

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
cugcauccuc cuggccaugt t                                                  21

<210> SEQ ID NO 8
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
cauggccagg aggaugcagt t                                                  21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 9
ggcuuucucc gcgguugact t                                                  21

<210> SEQ ID NO 10
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
gucaaccgcg gagaaagcct t                                              21

<210> SEQ ID NO 11
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
aaguguuuga ugcuggaggt t                                              21

<210> SEQ ID NO 12
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
ccuccagcau caaacacuut t                                              21

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
gcaccagcuu uucugccuut t                                              21

<210> SEQ ID NO 14
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 14
aaggcagaaa agcuggugct t                                              21

<210> SEQ ID NO 15
<211> LENGTH: 21
<212> TYPE: DNA
```

<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 15
acugcacaga gagacgacut t                                              21

<210> SEQ ID NO 16
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 16
agucgucucu cugugcagut t                                              21

<210> SEQ ID NO 17
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
gcaccagcuu uucugccuut t                                              21

<210> SEQ ID NO 18
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
aaggcagaaa agcuggugct t                                              21

<210> SEQ ID NO 19
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
agcagcaugc acaaugccut t                                              21

<210> SEQ ID NO 20
<211> LENGTH: 21

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
aggcauugug caugcugcut t                                          21

<210> SEQ ID NO 21
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 21
agccugaccu cacucuaact t                                          21

<210> SEQ ID NO 22
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 22
guuagaguga ggucaggcut t                                          21
```

TOPICAL ADMINISTRATION OF AT LEAST ONE DOUBLE-STRANDED RNA OLIGONUCLEOTIDE (DSRNA)

CROSS-REFERENCE TO PRIORITY/PCT/PROVISIONAL APPLICATIONS

This application is a continuation of U.S. application Ser. No. 11/001,085, filed Dec. 2, 2004, which claims priority under 35 U.S.C. §119 of FR-02/06796, filed Jun. 3, 2002, and of U.S. provisional application No. 60/386,720, filed Jun. 10, 2002, and is a continuation of PCT/FR 2003/001648, filed Jun. 2, 2003 and designating the United States (published in the French language on Dec. 11, 2003, as WO 2003/101376 A3; the title and abstract were also published in English), each hereby expressly incorporated by reference and each assigned to the assignee hereof.

BACKGROUND OF THE INVENTION

1. Technical Field of the Invention

The present invention relates to the administration of at least one double-stranded RNA oligonucleotide (dsRNA) via topical application and to compositions for topical administration which comprise at least one encapsulated double-stranded RNA oligonucleotide formulated into a physiologically acceptable medium therefor.

2. Description of Background and/or Related and/or Prior Art

A large number of substances are administered topically for compensating for or preventing certain aesthetic impairments or certain disorders of the skin or its appendages. Of these substances, those which exhibit true biological specificity are more particularly desired.

Thus, the greater the extent to which the substances exhibit a specific activity, such as a specific biological activity, the less likely it is that they will induce undesirable side effects. For example, preference will be given to formulating a substance whose action is targeted on an enzyme such as tyrosinase into a composition which seeks to clear the complexion or prevent undesirable pigmentation. Mention may also be made, by way of example, of formulating a substance which acts specifically on certain metalloproteinases or elastases into a composition for preventing aging.

To date, this problem of specificity has been resolved by administering native DNA or RNA oligonucleotides or antisense DNA. However, such application has its limitations.

Thus, including DNA, non-specific RNA or antisense DNA oligonucleotides (such as those described, for example, in WO 01/58918) in topical formulations has not enabled any desirable efficacy to be obtained. In particular, RNases on the surface of the skin degrade native RNA and it is not possible for the quantities reaching the target mRNAs to be sufficient to obtain the desired effect. Another limitation to administering single-stranded oligonucleotides such as those mentioned above is the risk of the oligonucleotide possibly undergoing secondary refolding (or secondary re-pairing). For this reason, administering single-stranded oligonucleotides (such as antisense DNA oligonucleotides) in vivo is frequently ineffective. Furthermore, the stability of the effects produced by single-stranded oligonucleotides in vivo is short because of the oligonucleotides being broken down rapidly intracellularly and having a short extracellular half-life in vivo (Khan A et al., *J. Drug Target*, 2000, 8, 319-334).

Thus a need continues to exist for a composition which resolves both the difficulties of administering active compounds in a targeted manner and the problem of specificity and which is suitable for topical application.

Double-stranded RNA oligonucleotides, also termed dsRNAs, have long been known to be present in plants and eukaryotic organisms (Haines D. S. et al., *J. Cell Biochem.*, 1991; 46:9-20); their role is to inhibit the expression of a specific gene (Fire A., *Trends in Genetic*, 1999; 15:358-363).

Using dsRNA for therapeutic purposes has been described in WO 01/36646, which proposes a method for inhibiting genes which are involved in diseases, in particular cancers. The examples of implementing this method propose inhibiting the expression of a gene in undifferentiated cells, such as embryonic cells, or oocytes, by intracellularly injecting dsRNA which is targeted at the gene to be inhibited. The objective is to obtain a systemic effect. The modes of administration envisaged concern general administrations.

Contrary to the pharmaceutical compositions which are proposed in this publication, a topical formulation should reach a specific differentiated cell while at the same time only acting at the superficial level, that is to say at the level of the skin or its appendages (dermis, epidermis and keratinized appendages), or even only at the surface of the skin by targeting the eukaryotic microorganisms which cover it. It is also possible to search for an effect on a specific skin cell type, such as a fibroblast, a melanocyte, a keratinocyte, a Langerhans cell or an endothelial cell which is involved in aesthetic impairments or particular dermatological disorders.

SUMMARY OF THE INVENTION

It has now surprisingly been found that double-stranded RNA oligonucleotides can be administered for specifically inhibiting the expression of certain proteins in differentiated cells, in particular skin cells, and therefore for formulating compositions suitable for external topical administration.

The present invention thus features topically administering at least one double-stranded RNA oligonucleotide which is active on differentiated cells such as the cells of the dermis and the epidermis (melanocytes, fibroblasts, keratinocytes, etc.).

Topical administration according to the invention both possesses the features mentioned above and makes it possible to ameliorate or overcome the difficulties which have thus far been encountered.

This invention specifically features the expression of proteins in the cells of the dermis and the epidermis or in eukaryotic microorganisms at the surface of the skin, with it being possible for the targeting of the cells to be effected, in particular, by selecting a coating which enables the double-stranded RNA oligonucleotides to spread in the cell which is targeted.

The double-stranded RNA oligonucleotides make it possible to specifically inhibit a gene (or several genes in the case of a composition which combines double-stranded RNA oligonucleotides which possess different sequences and which are targeted at mRNAs encoding different proteins).

Because of their duplex structure, the double-stranded RNA oligonucleotides are resistant to RNases (enzymes for degrading RNA); the oligonucleotides are not broken down at the surface of the skin.

Too, because of their duplex structure, these double-stranded RNA oligonucleotides are unable to undergo folding and self-pairing; in this way, the bioavailability of the active product, that is to say the quantity of double-stranded RNA oligonucleotide which produces the desired effect and which arises in the cells, is markedly improved and makes it possible to use lower quantities of double-stranded RNA oligonucleotide.

The compositions comprising the double-stranded RNA according to the invention are particularly suitable for cosmetic or dermatological administration since they make it possible to reach the target cell without an invasive mode of administration and are active without having to penetrate into the cell nucleus.

DETAILED DESCRIPTION OF BEST MODE AND SPECIFIC/PREFERRED EMBODIMENTS OF THE INVENTION

The cell machinery which induces inhibition of the expression of the corresponding mRNA is brought into play by means of a complex mechanism within the cytoplasm. Administering a double-stranded RNA oligonucleotide into a cell induces a phenomenon involving the post-transcriptional extinction of the mRNA which the oligonucleotide targets.

The molecular mechanism which is brought into play involves sequences of 21 to 23 nucleotides which are contained in the double-stranded RNA oligonucleotides and which are responsible for the specificity for the sequence of the mRNA. These double-stranded RNA oligonucleotides are also termed dsRNA or else siRNA (short interfering RNA, see Tuschl. T., *Chem. Biochem.*, 2001; 2:239-245). The mechanism involves a dsRNA-protein complex which is formed in an ATP-dependent manner and which initiates a reaction in which the targeted mRNA is broken down specifically (Nykanen A et al., *Cell*, 2001, 107, 309-321).

The present invention firstly features topical administration/application of at least one double-stranded RNA oligonucleotide which generally comprises at least 10 nucleotides, in particular from 12 to 40 nucleotides, preferably from 20 to 25 nucleotides; very particular preference is given to double-stranded RNA oligonucleotides which comprise from 21 to 23 nucleotides.

A "double-stranded RNA oligonucleotide" is understood as being a ribonucleic acid sequence which has a double-helical structure whose sequence is substantially identical to at least a part of the targeted messenger RNA.

These sequences of the double-stranded RNA oligonucleotides according to the invention are generally derived from endogenous sequences, that is to say they represent all or part of mammalian or eukaryotic microorganism nucleotide sequences. The sequence can be a gene sequence or a coding DNA (cDNA) sequence which is produced from mammalian-derived messenger RNA (mRNA) using reverse transcriptase, for example; the sequence can also be a sequence of a yeast gene.

In particular, when the double-stranded RNA oligonucleotide sequence corresponds to all or part of the sequence of a gene, preference is given to using the sequences of one or more exons of the gene concerned.

The double-stranded RNA oligonucleotides according to the invention can be double-stranded RNA oligonucleotides which comprise one or more nucleotides which have been modified by substitution, deletion or insertion, with these modifications being such that the sequence of the double-stranded RNA oligonucleotide enables the oligonucleotide to specifically recognize a fragment of the mRNA which is the target of the degradation mechanism.

The double-stranded RNA oligonucleotides may also have a modified skeleton which improves their stability, for example.

For example, the phosphodiester bonds of the natural RNA strands can be modified so as to include at least one nitrogen atom or sulfur atom. Furthermore, the double-stranded RNA oligonucleotides according to the invention can contain bases other than the 4 usual bases.

The double-stranded structure of the double-stranded RNA oligonucleotide can be obtained by pairing two single RNA strands which are complementary or else the double-stranded RNA oligonucleotide can be obtained by the folding and pairing of a unique "self-complementary" single RNA strand, that is to say a strand which comprises two fragments of complementary sequence which can pair by the single strand being folded to form a double helix.

"Double-stranded RNA oligonucleotide which is substantially identical to a gene fragment" is understood as meaning a double-stranded RNA oligonucleotide whose sequence possesses a degree of homology (percentage of nucleic acid bases which are identical between two sequences, see the calculation methods proposed by Atschul et al., *J. Molec. Biol.*, 1990, 215:403) with the fragment of said gene which is between 80 and 100% and preferably at least 90%.

In one preferred embodiment of the invention, the double-stranded RNA oligonucleotide exhibits unpaired ends of 2 to 6 nucleotides in length.

The double-stranded RNA oligonucleotide according to the invention can also be modified by the addition of a polyethylene glycol, as defined by Garrett et al. (*Bioorg. Med. Chem.*, 2000 July, 8(7): 19779-97), in order to improve the efficacy of its transfection into the host cell.

The double-stranded RNA oligonucleotides according to the invention can be synthesized manually or automatically using a large number of in vivo or in vitro synthesis methods.

The in vitro synthesis methods can be chemical or enzymic, for example using an RNA polymerase (T3, T7 or SP6 by way of example) which will transcribe a chosen DNA (or cDNA) sequence model.

A large number of techniques for synthesizing double-stranded RNA in vivo are described in the literature; they can be carried out in a variety of bacterial or higher organism cell types (Sambrook et al., *Molecular Cloning, A Laboratory Manual*, Second Edition (1989), DNA cloning, volume I and II, D. N. Glover (ed. 1985), *Oligonucleotide Synthesis*, M. J. Gaits (ed. 1984), *Nucleic Acid Hybridation*, B. D. Hames and S. J. Higgins (ed. 1984), *Transcription and Translation*, B. D. Hames and S. J. Higgins (ed. 1984), *Animal Cell Culture*, R. I. Freshney (ed. 1986), *Immobilised Cells and Enzymes*, IRL Press (1986), B. Pertal, *A Practical Guide to Molecular Cloning*, (1984), *Gene Transfer Vectors for Mammalian Cells*, J. H. Miller and M. P. Calos, Cold Spring Harbor Laboratory (ed. 1987), *Methods of Enzmmology*, vol. 154, Wu and Grossman, and 155, Wu, Mayer and Walker (1987), *Immunochemical Methods in Cell and Molecular Biology*, Academic Press, London, Scopes (1987), *Protein Purification: Principle and Practice*, $2^{nd}$ ed., Springer-Verlag, N.-Y. and *Handbook of Experimental Immunology*, vol. I-IV, C. D. Weir and C. C. Blackwell (1986)). See also the synthesis methods which are described in WO 01/36646 and WO 01/75164.

The sequences of the double-stranded RNA oligonucleotides which are employed are in each case selected, using any method of molecular biology, for a specific topical use. While the mRNAs of the biological targets which are of interest in the cosmetic or dermatological field can, by way of example, be the proteins which are described below, they can also be any mRNAs which encode other skin proteins.

It is also possible to use a combination of several double-stranded RNA oligonucleotides which possess different sequences, and each of which has a different activity, for the purpose, for example, of obtaining complementary or synergistic effects.

In particular, the present invention relates to the topical administration of at least one double-stranded RNA oligonucleotide which is able to inhibit the expression of a messenger RNA which encodes a protein which is expressed by a cell of the skin or of its appendages.

The present invention also features cosmetic compositions in which the double-stranded RNA oligonucleotide is able to inhibit the expression of a messenger RNA which encodes a protein which is expressed by a eukaryotic microorganism which is present at the surface of the skin or of the scalp.

In particular, the skin protein is a protein which is expressed by melanocytes and/or keratinocytes and/or fibroblasts and/or the endothelial cells or the resident immune cells, such as the Langerhans cells. The protein is preferably expressed by the keratinocytes.

The proteins and/or oligopeptides whose synthesis can be reduced or inhibited are those which are involved in the phenomena of cell differentiation or proliferation, such as:
the growth factors EGF, TNF-α, TGF, endothelin, NGF, HGF, IGF and VEGF;
cytokines, for example of the IL1, IL6, IL8, etc. type;
receptors of the EGFr, TGFr, PAR, PPAR, FXR, RXR, CB1R, CB2R, VR1, CRAB2, etc. type;
calcium-binding proteins of the calmodulin, CLP and CLSP type, and those of the S100 protein family such as S100A8, S100A9, S100A7, etc.;
calcineurin;
transglutaminases, for example transglutaminases 1, 3 or 5;
proteins ensuring intercellular cohesion/linkage, such as occludins, laminins, caveolins, desmogleins, desmocollins, corneodesmosins, plakoglobins, desmoplakins, etc.;
enzymes involved in post-translational modifications of proteins such as phosphatases or protein phosphatases, for example calcineurin, phosphorylases, protein kinases (e.g., PKC), glucosyl transferases, peptidyl-arginine-deiminases, etc.;
proteases (MMP, for example 1, 2, 3 and 9, elastases, aspartic acid proteases such as cathepsin-E and cathepsin-D, cystein proteases of the cathepsin-L, B or H type, cathepsin L2, SCCL, chymotrypsin equivalents, for example of the SCCE (kallicrein 7) type, trypsin-like, for example of the SCTE (kallicrein 5) type, urokinase, SASPase, caspase, more specifically caspase 14, calpains, proteases of the subtilisin-like proprotein convertase type which are involved in the hydrolysis of filaggrin, such as furin, PACE4, PC5/6 and PC7/8, proteases of the serine protease family of the transmembrane type, for example matriptase and/or their endogenous inhibitors such as TIMP, PAI1, PAI2, antileukoprotease, elafin, LEKTI, cystatin A, cystatin M/E, etc.;
exoglycosidases and endoglycosidases, for example of the heparanase type, hyaluronidases, chondroitinases, aspartyl glucosaminidase, B glycosidase, a glycosidases, etc., and their endogenous inhibitors;
enzymes of lipid metabolism, such as HMGCoA reductase, cholesterol sulfatases or sulfotransferases, sphingomyelinases, ceramidases, etc.;
tyrosinase, TRP-1 or TRP-2;
enzymes of eicosanoid metabolism, such as cyclooxygenases, lipoxygenases, phospholipases, 15-PGDH, etc.;
enzymes of hormonal metabolism, such as type I or type II 5α-reductase;
matrix proteins of the elastin, collagen, etc. type;
keratinocyte differentiation proteins of the cytokeratin type;
proteins involved in hydration of the skin such as filaggrin, aquaporins, etc.;
proteins involved in the antibacterial defenses of the skin, hBD2, hBD3, dermcidin, RNase 7, etc.;

Other nonlimiting examples of proteins or peptides whose expression and/or activity is intended to be inhibited are reported in *Textbook of Dermatology*, eds. R H Champion, J L Burton, D A Burns, S M Breathnach, sixth edition, 1998, Blackwell Science Ltd ISBN 0-632-03796-2.

The messenger RNA in the dermis whose expression can be reduced or inhibited can be that of the fibroblasts or of other cells which are present in the dermis, i.e., the cells of the blood vessels, the cells of the epidermal appendages (examples: sebocytes, sudoriparous glands, etc.) and the cells which are able to migrate into the dermis such as the cells which are involved in immunity or inflammation.

The proteins and/or oligopeptides whose synthesis can be reduced or inhibited are those which are involved in the phenomena of cell differentiation or proliferation, such as those described in the case of keratinocytes and, in addition:
the growth factors EGF, TGF, endothelin, NGF, HGF and FGF, etc.;
phosphatases;
transglutaminases;
phosphorylases;
proteins involved in the renewal of the extracellular matrix (proteases: MMP metalloproteases, serine proteases such as urokinase, tPA,
hyaluronidases);
structural proteins of the dermis such as collagen, or of the amorphous ground substance such as the proteoglycan proteins;
proteins involved in the maturation of the dermis such as lysyl oxidase and lysyl hydroxylase.

At the level of complex structures, such as the hair follicle, it is envisaged to administer a group of siRNAs, each of which is directed against a messenger which is known to encode a regulatory and/or structural protein of the hair shaft, in order to obtain the desired effect:
antigrowth: for example the proteins involved in the cell cycle, and/or IGF receptor and/or T4 thyroid receptor;
antiloss: for example the siRNAs which are directed against cytokines IL1, IL6, TNFalpha and MCP1 and/or MMP proteases, urokinase and/or lipoxygenase;
regrowth: for example the proteins involved in breaking down PGF2alpha and/or 5alpha reductase; proteins involved in morphogenesis such as alpha3beta1-integrin, betacatenin, laminin-10 and LEF-1;
shaping the hair shaft, such as curling or uncurling: for example, the proteins involved in differentiation of the hair shaft, such as acid or basic hair keratins and also the enzymes associated with crosslinking the proteins of the shaft (e.g.: thiol oxidoreductases and transglutaminases 3 and 5).

Reference may be made to Jamora C., DasGupta R., Kocieniewski P., Fuchs E., *Nature*, 2003 Mar. 20; 422(6929): 317-22 for a nonlimiting list of this type of proteins.

At the level of complex structures such as the sebaceous gland, it is envisaged administering a group of siRNAs, each of which is directed against proteins which are involved in synthesis of the sebum, such as HMGCoa reductase and squalene synthase.

In the case of all these cell types, it is possible to administer, according to the invention, siRNAs which are directed against the expression of pathological proteins and/or oligopeptides, in particular those linked to viral action (e.g., verrucal HPV)

or to cancerous cells, or those which are overexpressed in certain diseases. Mention may be made, for example, of certain cytokines (for example IL1, TNFalpha −308 and TNF-beta +252), receptor proteins (for example Toll-like receptors, TLRs), certain proteins involved in proliferation such as phosphatidylinositol 3 kinase, adhesion molecules (for example CDw60), proteases, in particular serine proteases (stratum corneum chimotrypsin enzyme, SCCE) or metalloproteases (in particular MMP-9 and MMP-19 involved in psoriasis), or else calcium-linked proteins (calmodulin-like serin protease, CLSP).

In the case of all these cell types, it is also possible, in accordance with the invention, to administer siRNAs which are directed against the expression of proteins and/or oligopeptides which are involved in the deactivation of a drug which is intended for treating the skin, for example detoxification proteins such as cytochrome P450 or cytochrome CYP2S1 in the case of psoriasis.

In the case of all these cell types, it is possible to administer, in accordance with the invention, siRNAs which are directed against the expression of proteins and/or oligopeptides which are induced by external deleterious changes, for example siRNAs which are directed against P2X purinergic receptor following mechanical/chemical impairment of the corneal barrier.

The microorganisms which are present at its surface, and in which it is possible to reduce or inhibit the synthesis of proteins and/or oligopeptides, are eukaryotes, such as yeasts and fungi. In a nonlimiting manner, representative are:

dermatophyte organisms which are the agents responsible for mycoses (trichophyton species, including *T. rubrum* and *T. mentagrophytes*). The dermatophytes are keratinophilic filamentous fungi, that is to say having a preferential tropism for the hair and nails and the corneal layer.

Three types of dermatophyte are responsible for dermatophytoses:

1. Anthropophilic dermatophytes: these are strictly of human origin.

Examples of these agents are:

*Trichophyton rubrum, Trichophyton interdigitale, Trichophyton violaceum, T. Rosaceeum, T. Tonsurans, T. Soudanensae, Trichophyton Schoenleinii, Epidermophyton Floccosum Microsporum Audouinii.*

2. Zoophilic dermatophytes which are transmitted to man by animals. Examples of the agents responsible are *Microsporum canis, Trichophyton Mentagrophytes* and *Trichophyton ochraceum.*

3. Geophilic dermatophytes, which are transmitted to man by the soil. The main agent is microsporum gypseum.

Nondermatophytes (the *Candida* species such as *C. albicans*, etc., the *Scopulariopsis* species such as *S. brevicaulis*, and *Malassezia* spp.). These are yeasts represented by the genus candida and by *Malassezia furfur* (formerly called pityrosporon). *Candida* affects the skin, the nails and hair and the mucous membranes. *Malassezia furfur*, which is a frequent saprophyte of the skin, especially seborrheic skin, is the agent of pityriasis versicolor. While it is entirely normal for particles of dead skin to become detached from the scalp as from the remainder of the skin, this permanent process of epidermal renewal can sometimes assume embarrassing proportions. While being unsightly, dandruff is also sometimes accompanied by more serious problems of the scalp such as irritation, redness and itching. This is then referred to as seborrheic dermatitis, a skin complaint which is promoted by the fungus *Pityrosporum ovale.*

Molds, which are less frequently involved in conditions of the corneal layer. They are responsible for certain onychomycoses and invasive mycoses.

According to the invention, specific proteins of these organisms such as *C. albicans* cytochrome P450-dependent 14-alphasterol demethylase and squalene epoxidase, proteins for detoxifying antimycotic agents, such as the *Trichophyton rubrum* esterases, aspartic proteinases, candida phospholipase B and phospholipase D, and 2,3-oxidosqualene cyclases such as 22,23-epoxy-2-aza-2,3-dihydrosqualene (EAS) and azasqualene alcohol (ASA) can be inhibited. A more complete list, by way of nonlimiting examples, of eukaryotic organisms will be found in *Textbook of Dermatology*, eds. R H Champion, J L Burton, D A Burns, S M Breathnach, sixth edition, 1998, Blackwell Science Ltd, ISBN 0-632-03796-2.

More generally according to the invention, the siRNAs are chosen and/or combined in accordance with the desired topical effect. With the prior art, a molecular method can be considered for streaming the messenger RNAs which are induced and/or repressed by a drug or as the result of undesirable effects (DNA array method) in order to determine the choice and the assembly of the siRNAs which correspond to the effect to be obtained and/or prevented.

The dsRNAs which are employed are in each case selected for a specific topical use using any suitable molecular biological method and such that this is done for each messenger RNA, in particular in accordance with its primary structure. The mRNAs of the biological targets which are of interest in cosmetics can, by way of example, and with this being in a nonlimiting list, be: tyrosinase, TRP-1, elastase, hyaluronidase, metalloprotease, HmoCoA reductase, 5 α-reductase, SCCE, NO synthase, urokinase, mRNAs for epidermal proteins, etc.

In one embodiment of the invention, a double-stranded RNA oligonucleotide is administered which is able to inhibit the expression of a messenger RNA which encodes tyrosinase. In particular, the double-stranded RNA oligonucleotide is such that the sequence of its 5' sense strand is SEQ ID no. 1: 5'-UGCACCACUUGGGCCUCAAdTdT and the sequence of its 5' antisense strand is SEQ ID no. 2: 5'-UUGAGGCCCAAGUGGUGCAdTdT.

Administration according to the invention can also comprise utilizing a double-stranded RNA oligonucleotide which is able to inhibit the expression of a messenger RNA which encodes TRP-1 (tyrosinase-related protein 1).

Such topical applications are suitable for depigmenting and/or bleaching the skin and/or the hair and nails.

Another embodiment of the invention employs a double-stranded RNA oligonucleotide which is able to inhibit the expression of a messenger RNA which encodes the enzyme neutrophil elastase.

In particular, the double-stranded RNA oligonucleotide is such that the sequence of its 5' sense strand is SEQ ID no. 3: 5'-CGGCUACGACCCCGUAAACdTdT and such that the sequence of its 5' antisense strand is SEQ ID no. 4: 5'-GUUUACGGGGUCGUAGCCGdTdT.

Such a topical application is useful to prevent and/or combat signs of skin aging such as the loss of firmness and/or suppleness of the skin and/or atrophy of the skin and/or the formation of wrinkles and fine lines.

Another embodiment of the invention uses a double-stranded RNA oligonucleotide which is able to inhibit the expression of a messenger RNA which encodes hyaluronidase.

Such a topical application is useful to prevent and/or combat signs of skin aging such as loss of firmness and/or suppleness of the skin and/or atrophy of the skin and/or the formation of wrinkles and fine lines.

Another embodiment of the invention uses a double-stranded RNA oligonucleotide which is able to inhibit the expression of a messenger RNA which encodes a metalloproteinase.

The metalloproteinases (MMPs) are described, in particular, in the article by Y. HEROUY et al., *European Journal of Dermatology*, no. 3, vol. 10, April-May 2000, pp. 173-180.

The metalloproteinase family thus consists of several well-defined groups which are based on their similarity in terms of structure and substrate specificity (see Woessner J. F., *Faseb Journal*, vol. 5, 1991, 2145). Among these groups, mention may be made of the collagenases which are intended to break down fibrillar collagens (MMP-1 or interstitial collagenase, MMP-8 or neutrophil collagenase, MMP-13 or collagenase 3 and MMP-18 or collagenase 4), gelatinases which break down type IV collagen or any form of denatured collagen (MMP-2 or gelatinase A (72 kDa) and MMP-9 or gelatinase B (92 kDa)), stromelysins (MMP-3 or stromelysin 1, MMP-10 or stromelysin 2 and MMP-11 or stromelysin 3), whose broad spectrum of activity is aimed at proteins of the extracellular matrix such as glycoproteins (fibronectin and laminin), proteoglycans, etc., matrilysin (MMP-7), metalloelastase (MMP-12) or else the membrane metalloproteinases (MMP-14, MMP-15, MMP-16 and MMP-17).

The metalloproteinases (MMPS) are members of a family of proteolytic enzymes (endoproteases) which possess a zinc atom which is coordinated to 3 cysteine residues and a methionine in their active site and which break down the macromolecular components of the extracellular matrix and the basement membranes at neutral pH (collagen, elastin, etc.). Being very widely distributed in the living world, these enzymes are present, but weakly expressed, in normal physiological situations such as the growth of the organs and the renewal of the tissues. However, in humans, their overexpression and their activation are linked to a large number of processes which involve the destruction and remodeling of the matrix. This leads, for example, to uncontrolled resorption of the extracellular matrix.

A topical administration of this nature is useful to prevent and/or combat signs of skin aging such as loss of firmness and/or suppleness of the skin and/or atrophy of the skin and/or the formation of wrinkles and fine lines; they are also suitable for inducing and/or stimulating growth of head hair and/or body hair and/or for retarding its loss.

In another embodiment of the invention, a double-stranded RNA oligonucleotide is administered which is able to inhibit the expression of a messenger RNA which encodes HMG-CoA reductase.

In particular, the double-stranded RNA oligonucleotide is such that the sequence of its 5' sense strand is SEQ ID no. 5: 5'-AGCCGCGAGGGUCGUCCAAdTdT and such that the sequence of its 5' antisense strand is SEQ ID no. 6: 5'-UUG-GACGACCCUCGCGGCUdTdT.

Such a topical administration is useful to prevent and/or combat the excessive production of sebum or sweat in the region of the armpits or the feet.

In another embodiment of the invention, a double-stranded RNA oligonucleotide is administered which is able to inhibit the expression of a messenger RNA which encodes type I and/or type II 5α-reductase, preferably type I 5α-reductase.

In particular, the double-stranded RNA oligonucleotide is such that the sequence of its 5' sense strand is SEQ ID no. 7: 5'-CUGCAUCCUCCUGGCCAUGdTdT and such that the sequence of its 5' antisense strand is SEQ ID no. 8: 5'-CAUG-GCCAGGAGGAUGCAGdTdT.

Such a topical administration is useful to treat androgen-dependent disorders, in particular to treat hyperseborrhea and/or acne and/or to induce and/or stimulate growth of head hair and/or body hair and/or retard loss of head hair.

In another embodiment of the invention, a double-stranded RNA oligonucleotide is administered which is able to inhibit the expression of a messenger RNA which encodes calmodulin-like skin protein (CLSP).

In particular, the double-stranded RNA oligonucleotide is such that the sequence of its 5' sense strand is SEQ ID no. 9: 5'-GGCUUUCUCCGCGGUUGACdTdT and such that the sequence of its 5' antisense strand is SEQ ID no. 10: 5'-GU-CAACCGCGGAGAAAGCCdTdT.

Such a topical administration is useful to combat the signs of skin aging and/or combat the harmful effects of ultraviolet rays and/or treat dry skin.

In another embodiment of the invention, a double-stranded RNA oligonucleotide is administered which is able to inhibit the expression of a messenger RNA which encodes NO synthase.

Such a topical administration is useful to inhibit cellular proliferation and/or differentiation and/or inhibit the breakdown and/or destruction of the cells of the skin and in this way combat intrinsic and/or extrinsic aging and/or retard loss of the hair. These compositions are also suitable for treating sensitive skin and erythemas, in particular light-induced erythemas.

In another embodiment of the invention, a double-stranded RNA oligonucleotide is administered which is able to inhibit the expression of a messenger RNA which encodes a serine protease such as urokinase. The compositions of this type are particularly suitable for cosmetic treatment and for improving the appearance of dry and/or irritated skin.

In other embodiments of the invention, a double-stranded RNA oligonucleotide is administered which is able to inhibit the expression of a messenger RNA encoding:

IL1, for its applications in the area of sensitive skin,
5α reductase, for its applications in the area of fatty skin,
a bacterial lipase, for its applications for combating dandruff formation, or else
lox12 and/or cox2 and/or IL1 and/or TGFβ1, for applications for combating hair loss.

For administration/application according to the invention, the double-stranded RNA oligonucleotide can be present in a composition at a concentration of from $5.10^{-7}$ to 5%, preferably of from 0.0001 to 1% of double-stranded RNA oligonucleotide(s) by weight based on the total weight of the composition.

Such a composition can be present in all the galenic forms which are normally employed for this type of application, in particular in the form of an aqueous or oily solution, of an oil-in-water or water-in-oil, or multiple, emulsion, of a siliconated emulsion, of a microemulsion or nanoemulsion, of an aqueous or oily gel or of an anhydrous liquid, pasty or solid product.

The present invention also features compositions suited to be applied topically and which comprise an encapsulated double-stranded RNA oligonucleotide formulated into a physiologically acceptable medium therefor.

In one preferred embodiment, the composition is such that the double-stranded RNA oligonucleotide is encapsulated in the core or the wall of a covering such as microspheres, nanospheres, oleosomes, niosomes or nanocapsules.

The double-stranded RNA oligonucleotides, at an effective molar concentration in an aqueous solution, can be complexed with a polyethylene imine (PEI) having a molecular weight of from 200 to 100 000 g/m. The nature of the PEI, and its proportion of from $10^{-4}$ to 1%, depend on the initial type of aqueous solution containing the double-stranded RNA oligonucleotides and on the cosmetic formulation intended. The opalescence of the initial solution can be used to indicate the formation of the complex.

Once the complex has been formed, it is encapsulated in particles, such as niosomes, which have an aqueous core or it is complexed on the surface of vesicles which have a lamellar surface which contains a polymer or a cationic lipophilic surfactant such as hydrophobic PEIs.

Thus, the double-stranded RNA oligonucleotide can be either:

complexed by a polycation (for example a hydrophilic PEI or chitosan);

By way of example, it is possible to select poly(4-vinylpyridine)-derived polycations (Modulation of interaction of polycations with negative unilamellar lipid vesicles, by Yaroslavov et al. in *Colloids and surfaces B:Biointerfaces*, 16 (1999)29-43); polymers and copolymers of lysine (cited in Turbidometric analysis of polyelectrolyte complexes formed between poly(L-lysine) and DNA, by Ward et al., in *Colloids and surfaces B:Biointerfaces*, 16 (1999)253-260); copolymers of quaternized vinylimidazole and vinylpyrrolidine such as the Luviquats from BASF (mw between 1000 and 1 000 000); chloride-based copolymers of diallyl dimethylammonium such as the Merquats from BASF (mw between 10 000 and 10 000 000); polyglucoseamines such as chitosan and its derivatives; polyamines such as polyethyleneimine which are or are not hydrophobic; guar derivatives such as the Jaguars from Rhodia; cationic cellulose derivatives such as the Celquats from National Starch or the Quarisofts from Amerchol; copolymers of vinylpyrrolidone and dimethylaminopropylmethacrylamide such as the Gafquats from ISP; cationic derivatives of acrylic acid such as HYPAN QT 100 from Kingston; the Salcare SC92, SC95 and 96 from Allied Colloide, and Plex4739L from Rohm Gmbh; derivatives of diurethane and polyurethane such as Polyderme PPI-SA, Foamox PPI-SA, Foamtaine PPI-SA15 and Foamquat PPI-SA from Alzo and copolyamines such as polyquart H-81 from Henkel;

this complex can then be encapsulated in particles having an aqueous core such as liposomes and, in particular, niosomes (see EP-0,582,503 or U.S. Pat. No. 5,439,672);

complexed on the surface of vesicles which possess a lamellar surface which contains a polymer or a cationic lipophilic surfactant.

In this latter case, the cationic lipophilic surfactants can be more particularly selected from the group consisting of quaternary ammonium salts and fatty amines and their salts.

Examples of the quaternary ammonium salts are:

(1)

in which the radicals $R_1$ to $R_4$, which can be identical or different, represent a linear or branched aliphatic radical having from 1 to 30 carbon atoms or an aromatic radical such as aryl or alkylaryl radicals. The aliphatic radicals can comprise heteroatoms such as, in particular, oxygen, nitrogen, sulfur and the halogens. The aliphatic radicals are selected, for example, from the radicals alkyl, alkoxy, polyoxy($C_2$-$C_6$) alkylene, alkylamide, ($C_{12}$-$C_{22}$)alkylamido($C_2$-$C_6$)alkyl, ($C_{12}$-$C_{22}$)alkyl acetate and hydroxyalkyl having from about 1 to 30 carbon atoms; X is an anion which is selected from the group of halides, phosphates, acetates, lactates, ($C_2$-$C_6$)alkyl sulfates and alkyl- or alkylaryl-sulfonates. Quaternary ammonium salts of the formula (II) which are preferred are, on the one hand, tetraalkylammonium chlorides such as dialkyldimethylammonium or alkyltrimethylammonium chlorides in which the alkyl radical comprises from about 12 to 22 carbon atoms, in particular the chlorides of behenyltrimethylammonium, of distearyidimethylammonium, of cetyltrimethylammonium of benzyldimethylstearylammonium, or else, on the other hand, the chloride of stearamidopropyldimethyl(myristyl acetate) ammonium, which is marketed by VAN DYK under the designation "CERAPHYL 70".

(2) The quaternary ammonium salts of imidazolinium, such as those of the following formula:

in which $R_5$ represents an alkenyl or alkyl radical having from 8 to 30 carbon atoms, for example derived from tallow fatty acids; $R_6$ represents a hydrogen atom, an alkyl radical having from 1 to 4 carbon atoms or an alkenyl or alkyl radical having from 8 to 30 carbon atoms; $R_7$ represents an alkyl radical having from 1 to 4 carbon atoms; $R_8$ represents a hydrogen atom or an alkyl radical having from 1 to 4 carbon atoms; X is an anion selected from the group consisting of halides, phosphates, acetates, lactates, alkyl sulfates and alkyl- or alkylarylsulfonates. Preferably, $R_5$ and $R_6$ denote a mixture of alkenyl or alkyl radicals having from 12 to 21 carbon atoms, for example derived from tallow fatty acids, $R_7$ denotes a methyl radical and $R_8$ denotes hydrogen. Such a product is marketed, for example, by REWO under the designation "REWOQUAT W 75".

(3) The quaternary diammonium salts of the formula:

in which $R_9$ denotes an aliphatic radical having from about 16 to 30 carbon atoms; $R_{10}$, $R_{11}$, $R_{12}$, $R_{13}$ and $R_{14}$ are each hydrogen or an alkyl radical having from 1 to 4 carbon atoms; and X is an anion which is selected from the group consisting of halides, acetates, phosphates, nitrates and methyl sulfates. These quaternary diammonium salts comprise, in particular, propanetallow diammonium dichloride.

The double-stranded RNA oligonucleotide can also be complexed on the surface of cationic oily globules whatever their size (see EP-1,010,413, EP-1,010,414, EP-1,010,415, EP-1,010,416, EP-1,013,338, EP-1,016,453, EP-1,018,363, EP-1,020,219, EP-1,025,898, EP-1,120,101, EP-1,120,102, EP-1,129,684, EP-1,160,005 and EP-1,172,077).

The double-stranded RNA oligonucleotide can also be complexed on the surface of nanocapsules or nanoparticles which are provided with a lamellar coating (see EP-0,447,318 and EP-0,557,489) and which contain a cationic surfactant at the surface (see the previously cited references for the cationic surfactants).

In particular, the vesicles which are preferred in accordance with the present invention are:

the niosomes described in EP-0,582,503;

the lipid spherules whose method of synthesis is described in U.S. Pat. No. 5,021,200;

the oil-in-water niosomes described in U.S. Pat. No. 5,489,426;

the nanoemulsions proposed in EP-0,879,589.

Preferred are the following lipids: PEI which is rendered hydrophobic by grafting on C10 to C22 alkyl chains (from 5 to 50%), which are unsaturated or saturated or branched or unbranched, stearylamine or behenyltriammonium chloride.

More particularly, preferred are vesicles which have a diameter which is less than or equal to 2 µm and is preferably between 50 nm and 1 µm.

It is also possible to use physical methods of intracutaneous administration such as a gas propulsion system or a microneedle patch.

Figure 1:
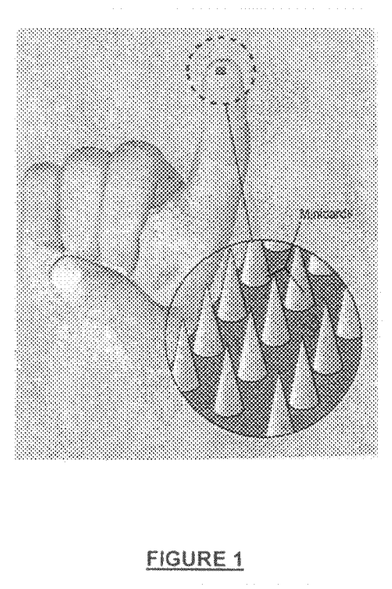
FIG. 1: depicts a microneedle patch which can be used for administering double-stranded RNA oligonucleotides.

In FIG. 1, which depicts a microneedle patch, the minidarts (cones) have a height which corresponds to the depth which the dsRNA which is encapsulated in a vesicle should reach (superficial epidermis, deep epidermis, superficial dermis, etc.). The size of the patch can, for example, be matched to the area of a pigment spot or a wrinkle.

In a more detailed manner, the composition which is applied topically can be more or less fluid and have the appearance of a white or colored cream, of an ointment, of a milk, of a lotion, of a serum, of a paste, of a mousse or of a gel. It can, where appropriate, be applied to the skin in the form of an aerosol. It can also be present in solid form and, for example, be in the form of a stick. It can be used as a care product and/or as a skin makeup product.

Thus, the compositions according to the invention can, in addition to the double-stranded RNA oligonucleotide, contain at least one active compound selected from: α-hydroxyacids; salicylic acid and its derivatives such as n-octanoyl-5-salicylic acid; HEPES; procysteine; O-octanoyl-6-D-maltose; the disodium salt of methylglycinediacetic acid; ceramides; steroids such as diosgenin and derivatives of DHEA; kojic acid; N-ethyloxycarbonyl-4-paraaminophenol; ascorbic acid and its derivatives; bilberry extracts; retinoids and, in particular, retinol and its esters; polypeptides and their acylated derivatives; phytohormones; extracts of the yeast *Saccharomyces cerevisiae*; algal extracts; extracts of *Vitreoscilla filiformis*; extracts of soybean, lupin, corn and/or pea; alverine and its salts, in particular alverine citrate; resveratrol; carotenoids and, in particular, lycopene; tocopherol and its esters; coenzyme Q10 or ubiquinone; xanthines and, in particular, caffeine and the natural extracts containing it; extracts of butcher's-broom and horse-chestnut; and their mixtures, without this list being limiting.

In addition, the compositions according to the invention can contain at least one UVA and/or UVB filter. The sunscreen filters can be selected from organic filters and inorganic filters and their mixtures.

Examples of organic filters which are active in the UV-A and/or the UV-B and which may in particular be mentioned are those designated below by their CTFA name:

derivatives of paraminobenzoic acid: PABA, ethyl PABA, ethyldihydroxypropyl PABA, ethylhexyldimethyl PABA, marketed, in particular, by ISP under the name "ESCALOL 507", glyceryl PABA, PEG-25 PABA, marketed by BASF under the name "UVINUL P25", salicylic derivatives: homosalate, marketed by RONA/EM INDUSTRIES under the name "EUSOLEX HMS", ethylhexyl salicylate, marketed by HAARMANN and REIMER under the name "NEO HELIOPAN OS", dipropyleneglycol salicylate, marketed by SCHER under the name "DIPSAL", TEA salicylate, marketed by HAARMANN and REIMER under the name "NEO HELIOPAN TS", derivatives of dibenzoylmethane: butylmethoxydibenzoylmethane, marketed, in particular, by HOFFMANN LA ROCHE under the trademark "PARSOL 1789", isopropyldibenzoylmethane, cinnamic derivatives: ethylhexyl methoxycinnamate, marketed, in particular, by HOFFMANN LA ROCHE under the trademark "PARSOL MCX", isopropylmethoxycinnamate, isoamylmethoxycinnamate, marketed by HMRMANN and REIMER under the trademark "NEO HELIOPAN E 1000", cinoxate, DEA methoxycinnamate, diisopropyl methylcinnamate, glyceryl ethylhexanoate dimethoxycinnamate, derivatives of β,β'-diphenylacrylate: octocrylene, marketed, in particular, by BASF under the trademark "UVINUL N539", etocrylene, marketed, in particular, by BASF under the trademark "UVINUL N35", derivatives of benzophenone: benzophenone-1, marketed by BASF under the trademark "UVINUL 400", benzophenone-2, marketed by BASF under the trademark "UVINUL D50", benzophenone-3 or oxybenzone, marketed by BASF under the trademark "UVINUL M40", benzophenone-4, marketed by BASF under the trademark "UVINUL MS40", benzophenone-5, benzophenone-6, marketed by NORQUAY under the trademark "HELISORB 11", benzophenone-8, marketed by AMERICAN CYANAMID under the trademark "SPECTRA-SORB UV-24", benzophenone-9, marketed by BASF under the trademark "UVINUL DS-49", and benzophenone-12, derivatives of benzylidene camphor: 3-benzylidene camphor, 4-methylbenzylidene camphor, marketed by MERCK under the name "EUSOLEX 6300", benzylidene camphor sulfonic acid, camphor benzalkonium methosulfate, terephthalylidene dicamphor sulfonic acid and polyacrylamidomethyl benzylidene camphor, derivatives of phenyl benzimidazole: phenylbenzimidazole sulfonic acid, marketed, in particular, by MERCK under the trademark "EUSOLEX 232", and benzimidazilate, marketed by HMRMANN and REIMER under the trademark "NEOHELIOPAN AP", derivatives of triazine: anisotriazine, marketed by CIBA GEIGY under the trademark "TINOSORB S", ethylhexyl triazone, marketed, in particular, by BASF under the trademark "UVINUL T150", and diethylhexyl-butamidotriazone, marketed by SIGMA 3V under the trademark "UVASORB HEB", derivatives of phenyl benzotriazole: drometrizole trisiloxane, marketed by RHODIA CHIMIE under the name "SILATRIZOLE", anthranilic derivatives: menthyl anthranilate, marketed by HMRMANN and REIMER under the trademark "NEO HELIOPAN MA", imidazoline derivatives: ethylhexyldimethoxy-benzylidenedioxoimidazoline propionate, derivatives of benzalmalonate: polyorganosiloxane having benzalmalonate functions, marketed by HOFFMANN LA ROCHE under the trademark "PARSOL SLX", and their mixtures.

The organic UV filters which are more particularly preferred are selected from among the following compounds:

ethylhexyl salicylate, butylmethoxydibenzoylmethane, ethylhexyl methoxycinnamate,
octocrylene,
phenylbenzimidazole sulfonic acid,
terephthalylidene dicamphor sulfonic,
benzophenone-3,
benzophenone-4,
benzophenone-5,
4-methylbenzylidene camphor,
benzimidazilate,
anisotriazine,
ethylhexyl triazone,
diethylhexylbutamidotriazone,
methylene bis-benzotriazolyl tetramethylbutylphenol,
drometrizole trisiloxane,
and their mixtures.

The inorganic filters which can be used in the composition according to the invention are, in particular, coated or uncoated metallic oxide nanopigments (mean size of the primary particles: in general, from 5 nm to 100 nm, preferably from 10 nm to 50 nm), such as nanopigments of titanium oxide (amorphous or crystallized in rutile and/or anatase form), of iron oxide, of zinc oxide, of zirconium oxide or of cerium oxide. Coating agents are, in addition, alumina and/or aluminum stearate. These coated or uncoated metallic oxide nanopigments are described, in particular, in EP-A,0-518,772 and EP-A,0-518,773.

In a known manner, the compositions of the invention can also contain adjuvants which are customary in the cosmetic and dermatological fields, such as hydrophilic or lipophilic gelatinizing agents, preservatives, antioxidants, solvents, surfactants, thickeners, perfumes, fillers, pigments, odor absorbers and coloring substances. The quantities of these adjuvants are those which are usually employed in the fields in question and are, for example, from 0.01 to 20% of the total weight of the composition. These adjuvants can be introduced, in accordance with their nature, either into the fatty phase or into the aqueous phase. These adjuvants, and their concentrations, should be such that they do not impair the advantageous properties of pantetheinesulfonic acid or its salts.

When the composition of the invention is an emulsion, the proportion of the fatty phase can range from 5% to 80% by weight, preferably from 5% to 50% of the total weight of the composition. The oils, the emulsifiers and the coemulsifiers which are used in the composition in emulsion form are selected from those which are usually employed in the field in question. The emulsifier and the coemulsifier are present, in the composition, in a proportion which ranges from 0.3% to 30% by weight, preferably from 0.5% to 20% of the total weight of the composition.

Examples of oils which can be used in the composition of the invention and which may be mentioned are:

hydrocarbonaceous oils of animal origin, such as perhydrosqualene;

hydrocarbonaceous oils of vegetable origin, such as liquid fatty acid triglycerides which comprise from 4 to 10 carbon atoms and the liquid fraction of karite butter;

synthetic esters and ethers of, in particular, fatty acids, such as the oils of the formulae $R^1COOR^2$ and $R^1OR^2$ in which $R^1$ represents the residue of a fatty acid comprising from 8 to 29 carbon atoms and $R^2$ represents a branched or unbranched hydrocarbon chain which contains from 3 to 30 carbon atoms, such as Purcellin's oil, isononyl isononanoate, isopropyl myristate, ethyl-2-hexyl palmitate, octyl-2-dodecyl stearate, octyl-2-dodecyl erucate, and isostearyl isostearate; hydroxylated esters such as isostearyl lactate, octylhydroxystearate, octyldodecyl hydroxystearate, diisostearylmalate, triisocetyl citrate, and heptanoates, octanoates and decanoates of fatty alcohols; polyol esters, such as propylene glycol dioctanoate, neopentylglycol diheptanoate and diethyleneglycol diisononanoate; and pentaerythritol esters, such as pentaerythrityl tetraisostearate;

linear or branched hydrocarbons of mineral or synthetic origin, such as volatile or nonvolatile paraffin oils and their derivatives, petrolatum, polydecenes, and hydrogenated polyisobutene such as parleam oil;

fatty alcohols having from 8 to 26 carbon atoms, such as cetyl alcohol and stearyl alcohol and their mixture (cetylstearyl alcohol), octyldodecanol, 2-butyloctanol, 2-hexyldecanol, 2-undecylpentadecanol, oleic alcohol or linoleic alcohol;

partially hydrocarbonaceous and/or siliconaceous fluorinated oils, such as those described in JP-A-2-295912;

silicone oils such as volatile or nonvolatile polymethylsiloxanes (PDMS) which have a linear or cyclic siliconaceous chain and which are liquid or pasty at ambient temperature, in particular cyclopoly-dimethylsiloxanes (cyclomethicones) such as cyclohexasiloxane; polydimethylsiloxanes which comprise alkyl, alkoxy or phenyl groups which are pendent or at the end of the siliconaceous chain, with the groups having from 2 to 24 carbon atoms; phenylated silicones such as phenyltrimethicones, phenyldimethicones, phenyl-trimethylsiloxydiphenylsiloxanes, diphenyldimethicones, diphenylmethyldiphenyltrisiloxanes, 2-phenylethyltrimethylsiloxysilicates and polymethylphenylsiloxanes;

their mixtures.

Examples of emulsifiers and coemulsifiers which can be used in the invention and which may be mentioned are O/W emulsifiers such as esters of fatty acid and polyethylene glycol, in particular PEG-100 stearate, and esters of fatty acid and glycerol, such as glyceryl stearate, as well as W/O emulsifiers such as the oxyethylenated poly(methylcetyl)(dimethyl)-methylsiloxane which is available from Degussa Goldschmidt under the trademark ABIL WE09, or the mixture of ethylene glycol acetyl stearate and glyceryl tristearate which is marketed by Guardian under the trademark UNITWIX.

Hydrophilic gelatinizing agents which may be mentioned, in particular, are carboxyvinylic polymers (carbomer), acrylic polymers such as acrylate/alkyl acrylate copolymers, polyacrylamides, polysaccharides, natural gums and clays, while lipophilic gelatinizing agents which may be mentioned are modified clays such as bentonites, metallic salts of fatty acids, hydrophobic silica and polyethylenes.

Examples of fillers which may be employed in the composition of the invention and which may be mentioned are, in addition to pigments, silica powder; talc; starch which is crosslinked with octenylsuccinic anhydride and which is marketed by National Starch under the designation DRY FLO PLUS (28-1160); polyamide particles, in particular those sold by Atochem under the designation ORGASOL; polyethylene powders; microspheres based on acrylic copolymers, such as those made of ethylene glycol dimethacrylate/lauryl methacrylate copolymer and sold by Dow Corning under the designation POLYTRAP; expanded powders such as hollow microspheres and, in particular, the microspheres marketed by Kemanord Plast under the designation EXPANCEL, or by Matsumoto under the designation MICROPEARL F 80 ED; silicone resin microbeads such as those marketed by Toshiba Silicone under the designation TOSPEARL; and their mixtures. These fillers can be present in quantities ranging from 0 to 20% by weight, and preferably of from 1 to 10% by weight, based on the total weight of the composition or of the preparation according to the invention.

One skilled in this art will take care to use ingredients and active compounds which do not impair the activity of the double-stranded RNA oligonucleotides which are present in the compositions according to the invention.

The present invention also features a cosmetic treatment method (regime or regimen) which comprises topically applying, to an area to be treated, a composition which comprises at least one double-stranded RNA oligonucleotide, as previously defined, in a physiologically acceptable medium. Advantageously, the composition is applied to the skin and/or the scalp and/or the hair and nails either once only or repeatedly over time.

The method can be a method for depigmenting and/or bleaching the skin or the nails and hair, with the method being characterized in that a composition according to the invention, in particular a composition which comprises a double-stranded RNA oligonucleotide which is able to inhibit the expression of a messenger RNA which encodes tyrosinase and/or a double-stranded RNA oligonucleotide which is able to inhibit the expression of a messenger RNA which encodes TRP-1, is applied to the area to be treated.

This invention also features a cosmetic treatment method for preventing and/or combating cutaneous signs of aging, with this method being characterized in that a composition comprising a double-stranded RNA oligonucleotide which is able to inhibit the expression of a messenger RNA which encodes neutrophil elastase and/or a double-stranded RNA oligonucleotide which is able to inhibit the expression of a messenger RNA which encodes hyaluronidase and/or a double-stranded RNA oligonucleotide which is able to inhibit the expression of a messenger RNA which encodes a metalloproteinase and/or a double-stranded RNA oligonucleotide which is able to inhibit the expression of a messenger RNA which encodes HMG-CoA reductase and/or a double-stranded RNA oligonucleotide which is able to inhibit the expression of a messenger RNA which encodes calmodulin-like skin protein (CLSP) and/or a double-stranded RNA oligonucleotide which is able to inhibit the expression of a messenger RNA which encodes NO synthase is applied to the area to be treated.

The present invention also features a cosmetic treatment method for inducing and/or stimulating growth of head hair and/or body hair and/or for retarding loss of head hair, with this method being characterized in that a composition comprising a double-stranded RNA oligonucleotide which is able to inhibit the expression of a messenger RNA which encodes a metalloproteinase and/or a double-stranded RNA oligonucleotide which is able to inhibit the expression of a messenger RNA which encodes type I or type II 5α-reductase and/or a double-stranded RNA oligonucleotide which is able to inhibit the expression of a messenger RNA which encodes NO synthase is applied to the area to be treated.

In order to further illustrate the present invention and the advantages thereof, the following specific examples are given, it being understood that same are intended only as illustrative and in nowise limitative. In said examples to follow, all parts and percentages are given by weight, unless otherwise indicated.

In these examples, reference will be made to the following figures of drawing.

EXAMPLE 1

Using RNA Interference to Inhibit the Expression of Tyrosinase

Materials and Methods:

The experimental conditions are those described by Tuschl et al. (*Journal of Cell Science*, 2001, 114, 4557-4565).

24 h before transfection, the melanocytes (MeWo cells) are sown, at the rate of 40,000 cells/well, in 500 μl of DMEM medium+10% serum in a 24-well plate. 0.84 μg or 2.52 μg of duplex siRNA (see description below), that is 60 pmol of tyrosinase siRNA in 3 μl of annealing buffer (Dharmacon) or, respectively, 180 pmol of tyrosinase siRNA in 9 μl of annealing buffer, are used per well. 3 μl or 9 μl of 20 μM tyrosinase duplex siRNA are diluted in 50 μl of Opti-MEM (Gibco). In another tube, 3 μl of oligofectamine (Invitrogen) are diluted in 12 μl of Opti-MEM and incubated at room temperature for 10 minutes. The 2 solutions are mixed and incubated at room temperature for 20 minutes before being added to the cells. The cells are then incubated at 37° C. for 96 h, with a change of medium after 24 h, and then lysed in a buffer containing 10 mM Tris-HCl, pH 7.2, 2% SDS, 1% Triton X-100, 10% glycerol+1% protease inhibitor; 34 μg of protein are then added, per well, to a polyacrylamide gel (NuPAGE Novex bis-Tris gels, *Invitrogen*), separated by electrophoresis and transferred by Western blotting in accordance with the supplier's instructions. The presence of tyrosinase on the membrane is analyzed by hybridizing with an antityrosinase antibody diluted 1/500 (NCL-TYR, *Novocastra*), and the quantity of protein which has been added is checked by hybridizing with an antivimentin antibody which has been diluted 1/40 000 (VIM3B4 clone, Cymbus Biotechnologies). The membrane is rinsed in PBS-Tween 20 and hybridized with a peroxidase-coupled antimouse secondary antibody (Goat antimouse-HRP, Dako) diluted 1/2000. Detection is effected using an "ECL Plus western blotting detection system" kit and following the supplier's (Amersham) instructions.

The following siRNA duplexes are selected from the sequence encoding human tyrosinase cDNA (accession number M27160). The adjacent number corresponds to the position of the $1^{st}$ nucleotide in the nucleic acid sequence. The duplexes are synthesized by Dharmacon or from DNA oligonucleotides provided by Proligo and transcribed into RNA using a "siRNA construction kit" (Ambion) and following the supplier's instructions. The 7 duplexes comprising an RNA sense strand and an RNA antisense strand consist of the following sequences, where AUG are ribonucleic acid bases and dT is a deoxyribonucleic acid base:

```
siRNA-TYR266 duplex:
siRNA 5' sense strand (SEQ ID N° 1):        UGCACCACUUGGGCCUCAAdTdT
siRNA 5' antisense strand (SEQ ID N° 2):    UUGAGGCCCAAGUGGUGCAdTdT siRNA-TYR359 duplex:
siRNA 5' sense strand (SEQ ID N° 11):       AAGUGUUUGAUGCUGGAGGdTdT
siRNA 5' antisense strand (SEQ ID N° 12):   CCUCCAGCAUCAAACACUUdTdT siRNA-TYR690 duplex:
siRNA 5' sense strand (SEQ ID N° 13):       GCACCAGCUUUUCUGCCUUdTdT
siRNA 5' antisense strand (SEQ ID N° 14):   AAGGCAGAAAAGCUGGUGCdTdT
```

-continued

```
siRNA-TYR832 duplex:
siRNA 5' sense strand (SEQ ID N° 15):      ACUGCACAGAGAGACGACUdTdT
siRNA 5' antisense strand, (SEQ ID N° 16): AGUCGUCUCUCUGUGCAGUdTdT siRNA-TYR110 duplex:
siRNA 5' sense strand (SEQ ID N° 17):      GCACCAGCUUUUCUGCCUUdTdT
siRNA 5' antisense strand (SEQ ID N° 18):  AAGGCAGAAAAGCUGGUGCdTdT siRNA-TYR1578 duplex:
siRNA 5' sense strand (SEQ ID N° 19):      AGCAGCAUGCACAAUGCCUdTdT
siRNA 5' antisense strand (SEQ ID N° 20):  AGGCAUUGUGCAUGCUGCUdTdT siRNA-TYR2120 duplex:
siRNA 5' sense strand (SEQ ID N° 21):      AGCCUGACCUCAGUCUAACdTdT
siRNA 5' antisense strand (SEQ ID N° 22):  GUUAGAGUGAGGUCAGGCUdTdT
```

Figure 2:
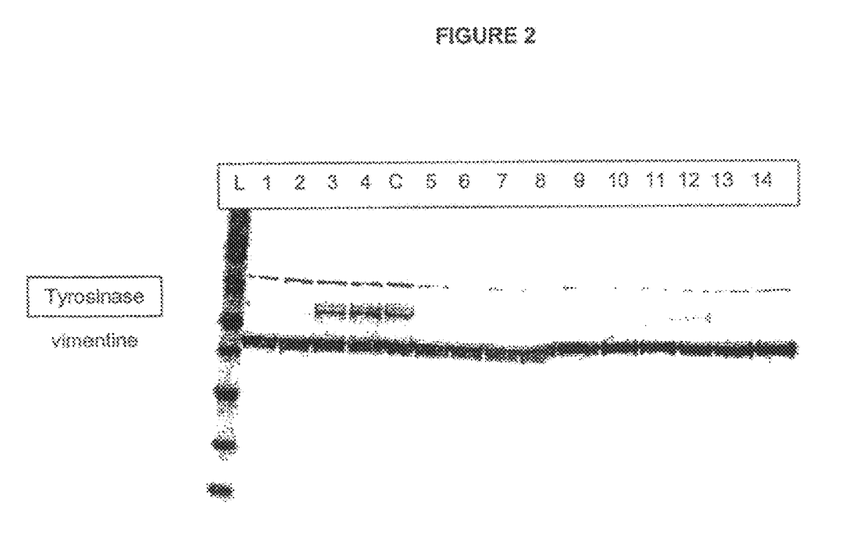
FIG. 2: specific extinction, by RNA interference, of the expression of tyrosinase in human melanocytes (MeWo).

The results are depicted in FIG. 2.
The lanes correspond to the following products:
L: molecular weight ladder
C: MeWo control
1: MeWo+TYR266 siRNA, 0.84 µg
2: MeWo+TYR266 siRNA, 2.52 µg
3: MeWo+TYR359 siRNA, 0.84 µg
4: MeWo+TYR359 siRNA, 2.52 µg
5: MeWo+TYR690 siRNA, 0.84 µg
6: MeWo+TYR690 siRNA, 2.52 µg
7: MeWo+TYR832 siRNA, 0.84 µg
8: MeWo+TYR832 siRNA, 2.52 µg
9: MeWo+TYR1110 siRNA, 0.84 µg
10: MeWo+TYR1110 siRNA, 2.52 µg
11: MeWo+TYR1578 siRNA, 0.84 µg
12: MeWo+TYR1578 siRNA, 2.52 µg
13: MeWo+TYR2120 siRNA, 0.84 µg
14: MeWo+TYR2120 siRNA, 2.52 µg The extinction of tyrosinase expression is confirmed by Western blotting. It appears that, of the 7 duplexes selected, 1 duplex is ineffective (359 siRNA), while 1 duplex is weakly effective (1578 siRNA) and the other 5 duplexes are functional, with what is apparently very powerful efficacy in the case of duplexes 1110 and 2120, as is demonstrated by the failure to detect tyrosinase. Specific inhibitors of tyrosinase are thus used to inhibit, by means of "RNA interference", the expression of proteins by epidermal cells.

EXAMPLE 2

Compositions

Composition 1: the Double-Stranded RNA Oligonucleotide is Complexed on the Surface of Cationic Vesicles:
Preparing the Vesicles:

| | |
|---|---|
| PEG 400 isostearate | 8% |
| Polyethyleneimine (PEI of 200 to 100000 MW) amidified with isostearic acid | 2% |
| Distilled water | qs for 100% |

Double-stranded RNA oligonucleotides of SEQ ID No. 1 and SEQ ID No. 2, with a dsRNA/PEI ratio of between 0.1 and 1000.

Steps Involved in Preparing Vesicles:
solubilizing the lipids in a methanol/chloroform mixture;
evaporating the solvent in a rotary evaporator under reduced pressure in order to obtain a lipid film;
hydrating the film while ultrasonicating;
checking the diameter of the vesicles (less than 1 µm; preferably 200 nm);
adding the solution of double-stranded RNA oligonucleotides.

Cosmetic Composition:
The vesicles are then incorporated into a cosmetic formulation which is suitable for topical application.
Daily application, preferably in the evening, of this preparation attenuates pigmentary spots; regular and long-term application leads to the disappearance of these pigmentary spots.

Composition 2: the dsRNA is Complexed in the Interior of Cationic Vesicles:
A) Encapsulating a Polycation/Double-Stranded RNA Oligonucleotides Complex:

| | |
|---|---|
| POE (8) stearate | 5.5% |
| Cholesterol | 4% |
| Polyethyleneimine (200 to 100000 MW), amidified with isostearic acid | 0.5% |

Aqueous solution A: distilled water, 30%, PEI (200 to 100000 MW), 1%, and double-stranded RNA oligonucleotide, QS to make up.
Aqueous solution B: distilled water, qs for 100%

B) Steps for Preparing the Vesicles:
See the preparation of composition 1. In this case, the hydration step is effected with ultrasonication, at the temperature which is suitable for the lipid mixture and with solution A, and a step of diluting with aqueous solution B is then added.

Cosmetic Composition:
The vesicles are then incorporated into a cosmetic formulation which is suitable for a topical application.
In this manner, compositions 1 and 2 can then be introduced, in a manner which is customary to one skilled in the art, into the following formulation. The ingredients are identified in accordance with the CTFA nomenclature.

| | |
|---|---|
| Glycerol | 5% |
| Preservatives | 1% |
| Disodium EDTA | 0.2% |
| Carbomer | 0.5% |
| Triethanolamine | 0.25% |
| Ammonium polyacryloyldimethyltaurate* | 0.3% |
| Sodium hyaluronate | 0.1% |
| Vegetable oils | 3% |
| Acrylamide/sodium acryloyldimethyltaurate and isododecane and polysorbate-80** | 2% |
| Cyclopentasiloxane and dimethiconol | 3% |
| Vesicle suspension in accordance with example 1 or 2 | 1 to 25% |
| Water | qs for 100% |

*Hostacerin AMPS supplied by CLARIANT
**Simulgel 600 supplied by SEPPIC

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A regime or regimen for inhibiting the expression of a messenger RNA which encodes a protein which is expressed by differentiated cells of the skin or appendages thereof, comprising topically administering to skin or appendages thereof an effective amount of at least one double-stranded RNA oligonucleotide complexed by a polycation, said complex being encapsulated in particles or being complexed on the surface of vesicles which have a lamellar surface, formulated into a topically applicable, physiologically acceptable medium therefor.

2. The regime or regimen as defined by claim 1, said at least one double-stranded RNA oligonucleotide comprising at least 10 nucleotides.

3. The regime or regimen as defined by claim 1, said at least one double-stranded RNA oligonucleotide comprising from 12 to 40 nucleotides.

4. The regime or regimen as defined by claim 1, said at least one double-stranded RNA oligonucleotide comprising from 20 to 25 nucleotides.

5. The regime or regimen as defined by claim 1, said at least one double-stranded RNA oligonucleotide comprising from 21 to 23 nucleotides.

6. The regime or regimen as defined by claim 1, said at least one double-stranded RNA oligonucleotide having been obtained by the folding and pairing of a self-complementary RNA single strand.

7. The regime or regimen as defined by claim 1, said at least one double-stranded RNA oligonucleotide having unpaired ends of from 2 to 6 nucleotides in length.

8. A regime or regimen as defined by claim 1 comprising depigmenting and/or bleaching the skin or the hair and nails of an individual in need of such treatment by topically administering to said-skin or appendages thereof an effective amount of at least one double-stranded RNA oligonucleotide complexed by a polycation, said at least one double-stranded RNA oligonucleotide inhibiting the expression of a messenger RNA which encodes tyrosinase and/or TRP-1.

9. A regime or regimen as defined by claim 1 for preventing and/or combating cutaneous signs of aging of an individual in need of such treatment, said at least one double-stranded RNA oligonucleotide inhibiting the expression of a messenger RNA which encodes neutrophil elastase and/or hyaluronidase and/or a metalloproteinase and/or HMG-CoA reductase and/or calmodulin-like skin protein (CLSP) and/or NO synthase.

10. A regime or regimen as defined by claim 1 for inducing and/or stimulating growth of head hair and/or body hair and/or retarding loss of head hair of an individual in need of such treatment, said at least one double-stranded RNA oligonucleotide inhibiting the expression of a messenger RNA which encodes a metalloprotease and/or type I or type II 5α-reductase and/or NO synthase.

11. A regime or regimen as defined by claim 1 for preventing and/or combating the loss of firmness and/or suppleness of the skin and/or atropy of the skin and/or the formation of wrinkles and fine lines of an individual in need of such treatment, said at least one double-stranded RNA oligonucleotide inhibiting the expression of a messenger RNA which encodes the enzyme neutrophil elastase, hyaluronidase or a metalloprotease.

12. A regime or regimen as defined by claim 1 for preventing and/or combating excessive production of sebum or sweat in the region of the armpits or the feet of an individual in need of such treatment, said at least one double-stranded RNA oligonucleotide inhibiting the expression of a messenger RNA which encodes HMG-CoA reductase.

13. A regime or regimen as defined by claim 1 for treating an androgen-dependent disorder of an individual in need of such treatment, said at least one double-stranded RNA oligonucleotide inhibiting the expression of a messenger RNA which encodes type I α-reductase.

14. A regime or regimen as defined by claim 1 for treating hyperseborrhea and/or acne of an individual in need of such treatment, said at least one double-stranded RNA oligonucleotide inhibiting the expression of a messenger RNA which encodes type I α-reductase.

15. A regime or regimen as defined by claim 1 for combating the harmful effects of ultraviolet radiation and/or treating dry skin of an individual in need of such treatment, said at least one double-stranded RNA oligonucleotide inhibiting the expression of a messenger RNA which encodes calmodulin-like skin protein (CLSP).

16. A regime or regimen as defined by claim 1 for inhibiting cellular proliferation and/or differentiation and/or inhibiting the breakdown and/or destruction of the cells of the skin of an individual in need of such treatment, said at least one double-stranded RNA oligonucleotide inhibiting the expression of a messenger RNA which encodes NO synthase.

17. A regime or regimen as defined by claim 1 for treating sensitive skin and erythemas of an individual in need of such treatment, said at least one double-stranded RNA oligonucleotide inhibiting the expression of a messenger RNA which encodes NO synthase.

18. A regime or regimen as defined by claim 1 comprising inhibiting the expression of a messenger RNA which encodes a protein expressed by melanocytes and/or keratinocytes and/or fibroblasts and/or endothelial cells and/or resident immune cells by said step of topically administering to skin or appendages thereof an effective amount of at least one double-stranded RNA oligonucleotide complexed by a polycation.

19. A regime or regimen as defined by claim 1 comprising inhibiting the expression of a messenger RNA which encodes a protein selected from the group consisting of tyrosinase, TRP-1 (tyrosinase-related protein 1), the enzyme neutophil elastase, hyaluronidase, a metalloproteinase, HMG-CoA reductase, type I or type II 5α-reductase, calmodulin-like skin protein (CLSP), NO synthase, urokiinase, cyclooxygenases, lipoxygenases, phospholipases, 15-PGDH, enzymes of hormonal metabolism, type I or type II 5α-reductase, matrix proteins of the elastin or collagen type, keratinocyte differentiation proteins of the cytokeratin type, proteins involved in moisturization of the skin, filaggrin, aquaporins, a serine protease, a cytokine, a growth factor, a protein or a peptide of morphogenesis, proteins involved in the antibacterial defenses of the skin, hBD2, hBD3, dermcidin, and RNase 7 by said step of topically administering to said-skin or appendages thereof an effective amount of at least one double-stranded RNA oligonucleotide complexed by a polycation.

20. A regime or regimen as defined by claim 1 for inhibiting the expression of a messenger RNA which encodes a protein of a eukaryotic microorganism selected from the group consisting of squalene epoxidase, C. albicans cytochrome P450-dependent 14-alpha sterol demethylase, proteins for detoxifying antimycotic agents, trichophyton rubrum esterases, aspartic proteinases, phospholipase D, Candida phospholipase B, 2,3-oxidosqualene cyclases, 22,23-epoxy-2-aza-2,3-dihydrosqualene (EAS) and azasqualene alcohol (ASA).

21. A regime or regimen as defined by claim 1 for treating psoriasis of an individual in need of such treatment, said at least one double-stranded RNA oligonucleotide inhibiting the expression of a messenger RNA which encodes a metalloprotease and/or a detoxification protein.

\* \* \* \* \*